United States Patent [19]
Vincent et al.

[11] 4,166,117
[45] Aug. 28, 1979

[54] 1-(ARALKYL)-4-(4-OXO[3H]QUINAZOLIN-3-YL)PIPERIDINES

[75] Inventors: Michel Vincent, Bagneux; Georges Remond, Versailles; Michel Laubie, Vaucresson, all of France

[73] Assignee: Science Union et Cie, France

[21] Appl. No.: 814,482

[22] Filed: Jul. 11, 1977

[30] Foreign Application Priority Data

Jul. 14, 1976 [GB] United Kingdom ............... 29317/76

[51] Int. Cl.² .................. A61K 31/505; C07D 455/02
[52] U.S. Cl. .................................... 424/251; 544/284; 544/287; 546/224; 260/651 F
[58] Field of Search ................. 260/256.4 Q; 424/251; 544/284, 287

[56] References Cited

U.S. PATENT DOCUMENTS

| | | | |
|---|---|---|---|
| 2,694,711 | 11/1954 | Baker et al. | 260/256.4 Q |
| 3,086,910 | 4/1963 | Shetty et al. | 260/256.4 Q |
| 3,257,397 | 6/1966 | Bolger | 260/256.4 Q |
| 4,027,028 | 5/1977 | Vincent et al. | 424/267 |

*Primary Examiner*—Paul M. Coughlan, Jr.
*Attorney, Agent, or Firm*—Gordon W. Hueschen

[57] ABSTRACT

This invention relates to novel quinazolinones, the nitrogen of which is bound to 4-amino piperidinyl-1 structures.

This invention also relates to processes for producing these compounds.

They have interesting pharmacological properties which make them useful in human or veterinary medicine for treating hypertension.

23 Claims, No Drawings

1-(ARALKYL)-4-(4-OXO[3H]QUINAZOLIN-3-YL)PIPERIDINES

PRIOR ART

The prior art may be illustrated by the following references:
French drug patent Nos. 2429, 2430 and 2431
British Pat. No. 1,345,872
U.S. Pat. No. 3,910,931
Belgian Pat. No. 615,350
U.S. Pat. No. 4,027,028 (to Vincent and al.)

SUMMARY OF THE INVENTION

This invention relates to N-substituted quinazolinones and more particularly to N-piperidino quinazolones.

Specifically, it provides new quinazolinones having the formula I:

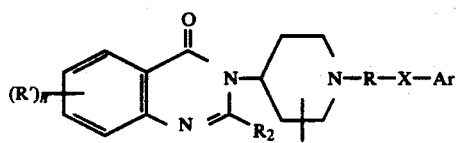

in which
Ar is an unsubstituted or substituted phenyl ring, a bicyclic radical selected from the group consisting of benzimidazolyl, indolyl, quinazolyl, dihydrobenzopyridyl and tetrahydrobenzopyridyl, and X is oxygen, sulphur or a substituted or unsubstituted amino group.

Another object of this invention is to provide the acid addition salts thereof with a mineral or organic acid, preferably a therapeutically-compatible acid.

A further object of this invention is to provide the optically-active isomers of the compounds having the formula I as far they contain at least one asymmetric carbon atom.

A further object of this invention is to provide a process for producing the compounds having the formula I from a piperidone, the carbonyl function thereof being protected by formation of a ketal or a cyclic ketal.

This invention also relates to pharmaceutical compositions containing as active ingredient at least one compound having the formula I or a salt thereof in admixture with a non-toxic inert pharmaceutical carrier suitable for oral, parenteral, rectal, sublingual ways.

The pharmaceutical compositions according to the invention are intended for the human or veterinary medicine, namely for treating hypertension in humans and in the animals.

PREFERRED EMBODIMENTS

The object of the present invention is to provide new N-substituted quinazolines. More particularly, it provides new (4-piperidinyl) quinazolines.

Specifically, it provides 4-(quinazolinon-4-yl) N-aralkyl piperidines of the general formula I:

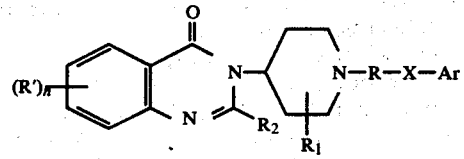

wherein Ar is a phenyl radical, a thienyl radical, a substituted phenyl radical having the general formula:

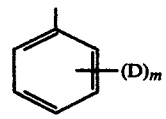

in which
D is selected from the group consisting of halogen, lower alkyl, lower alkoxy, lower alkenyloxy, lower alkynyloxy, a lower alkylthio, a carboxyl, a lower alkoxy carbonyl, a nitro group, an amino, a (lower alkyl) amino, a lower acylamino, a sulphamido, a lower alkylamino sulfonyl, a di (lower alkyl) amino sulfonyl, a lower alkyl sulfonyl, an amino carbonyl, a cyano and a trifluoromethyl,
m is an integer of 1 to 5,
or Ar is a heterobicyclic radical having the formula:

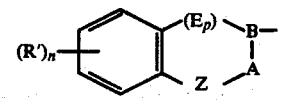

in which
R' is a radical selected from the group consisting of a hydroxyl, a lower alkoxy, a lower alkylenedioxy, a halogen, a trifluoromethyl, a trifluoromethoxy, a trifluoromethylthio, a nitro, an amino, a phenyl and a phenyl lower alkyl,
Z is a radical —N=,
A is an unsubstituted methylidene or a methylidene radical substituted with a lower alkyl,
B is an imino —NH— radical,
E is a carbonyl and
p is 1;
either Z is an imino radical —NH—, A and B together are an ethylidene radical, E is a methylene and p is zero or 1,
or Z is an imino radical —NH—, E is a methylene, p is zero or 1, A is a carbonyl grouping and B is an imino radical —NH— or A and B together are an ethylene radical.
X is an oxygen atom, a sulphur atom, or an imino radical of the formula:

wherein
Y is a hydrogen, a lower alkyl, a lower alkenyl or a lower alkoxy carbonyl, or
X is a methylene radical or a direct carbon-carbon bond, R is an alkylene radical having 1 to 4 carbon atoms, optionally substituted with a lower alkyl radical or a trifluoromethyl radical, R₁ is a hydrogen or a lower alkyl radical, R₂ is a hydrogen or a lower alkyl radical, n and n' distinctly are integers of zero to 3.

This invention also provides the salts of a compound of general formula I with a mineral or organic acid, preferably a therapeutically compatible acid.

This invention further provides optically-active isomers of the compounds of general formula I, when the chemical structure includes at least one asymetric carbon.

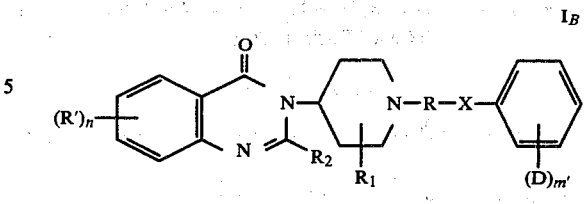

in which the substituents n, R', R, R₁, R₂, D and X are defined as above-given, and m' is an integer of zero to 5, (c) the compounds of general formula $I_C$ in which Ar is a quinazolinonyl ring

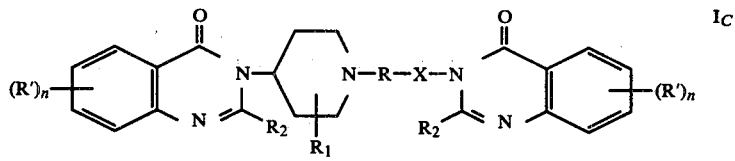

Moreover, when R₁ is a lower alkyl radical, the carbon atom in position 4 of the piperidine ring is asymetric and gives rise to the formation of geometric isomers which may separated and isolated.

in which the substituents n, R', R, R₁, R₂ and X have the previously given meanings, (d) the compounds of general formula $I_D$ in which Ar is an indolyl ring

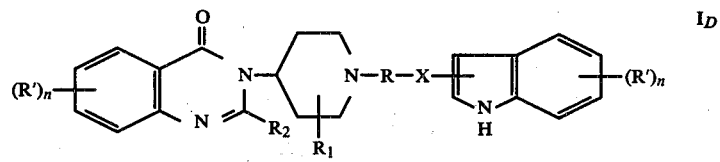

in which the definitions of the substituents n, R', R, R₁, R₂ and X are the same as above, and the indolyl ring is linked to X through the carbon 2 or the carbon 3 of the indolyl ring, Among the compounds of general formula I, several subgenuses may be shown and more precisely:

(a) the compounds of general formula $I_A$ in which Ar is a thienyl radical (e) the compounds of general formula $I_E$ in which Ar is a benzimidazolonyl ring

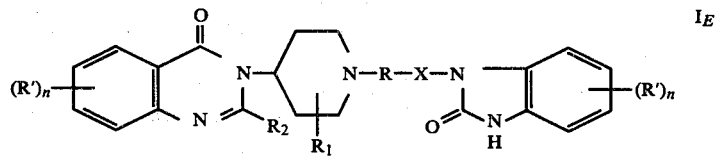

in which the substituents n, R', R, R₁, R₂ and X are defined as above.

In a preferred manner, the quinazolon-4-yl ring is unsubstituted in the phenyl ring or substituted with one or two substituents and the preferred quinazolones are those having the partial formula:

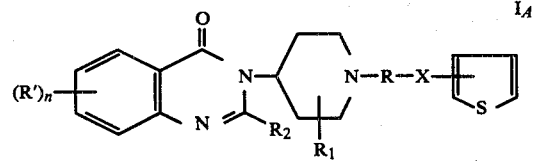

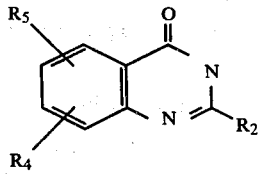

wherein the substituents R', R₁, R₂, R, X and n are defined as above-given, and X is bound to the thienyl ring in position (2) or (3)

(b) the compounds of general formula $I_B$ in which Ar is a phenyl or a substituted phenyl radical wherein R₄ and R₅, the same or different, are a hydrogen, a halogen, a hydroxyl, a lower alkyl, a lower alkoxy, a phenyl, a phenyl lower alkyl, a trifluoromethyl, a nitro group, an amino, or R₄ and R₅ together are a lower alkylene dioxy grouping of the formula —O—(CH₂)ₚ—O (in which p is 1, 2 or 3)

and R₂ is a hydrogen or a lower alkyl radical.

The compounds of general formula I as well as their acid addition salts, are endowed with interesting pharmacological properties, more particularly anti-hypertensive properties. They present a weak toxicity even intravenously and therefrom their safety margins are significant.

Therefore, they find in human and veterinary therapy a use as a drug for treating hypertension.

In contrast to previously known 4-amino piperidines, they are devoid at a significative degree of any depressive action of the central respiratory center in the brain. They are not analgetic and they are not antagonized by known antagonists of the morphinic alcaloids.

Due to their pharmacological properties, the following compounds are presently the preferred ones:

dl 1-[4-trifluoro 3-(phenyl butyl)]4-[4-oxo[3H]quinazolin-3-yl]piperidine.

1-(2-phenyl butyl)4-[4-oxo[3H]quinazolin-3yl]piperidine.

1-[3-(m.trifluoromethylphenyl)propyl-2]4-[4-oxo[3H-]quinazolin-3-yl]piperidine.

1-[2-(2,6-dimethyl phenoxy)ethyl]4-[6-chloro 4-oxo[3H-]quinazolin-3-yl]piperidine.

dl 1-(2-phenyl 1-methyl ethyl)4-[4-oxo[3H]quinazolin-3-yl]piperidine.

1-(3-phenylethyl)4-[4-oxo 6-methoxy[3H]quinazolin-3-yl]piperidine.

1-[2-(4-fluorophenyl)ethyl]4-[4-oxo[3H]quinazolin-3-yl]piperidine, and

1-[2-(indolyl-3)ethyl]4-[4-oxo[3H]quinazolin-3-yl]piperidine.

This invention provides the pharmaceutical compositions including as active ingredient at least one compound of general formula I or a salt thereof, in admixture with an inert, non toxic pharmaceutically-acceptable carrier.

For this therapeutic use, in human or veterinary medicine, the pharmaceutical compositions are those intended for parenteral, oral, sublingual or rectal administration. The most relevant examples are particularly tablets, coated tablets, capsules, dragees, granules, granulates, drops, drinkable suspensions or solutions, injectible solutions packed in ampuls, phials, multidosis flasks or auto-injectible syringes, suppositories, sublingual tablets and the like.

The useful posology may broadly vary depending on the age and weight of the patient, the therapeutic use and the route of administration. It may range from 5 mg and 50 mg per unit dosage and from 5 mg and 100 mg per day, in the man.

This invention also provides pharmaceutical compositions incorporating another active ingredient having an activity similar to that to the compounds of general formula I, complementary or synergistic.

The carriers suitable for the production of the pharmaceutical compositions according to this invention may be kaolin, talc, magnesium stearate, methyl cellulose, ethyl cellulose, distilled water, cocoa butter or polyethylene glycol stearates.

The pharmaceutical compositions are produced according to the methods previously known in the pharmacotechnology.

The present invention further provides a process for producing a compound of general formula I:

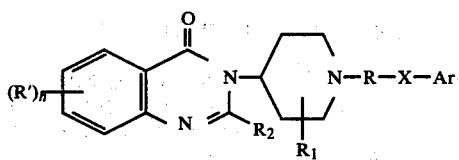

in which the substituents n, R', R₁, R₂, R, X and Ar are defined as previously indicated, in which a ketal of piperidone having the general formula II:

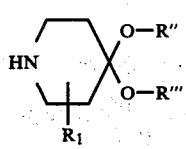

wherein R" and R''', the same or different, are a lower alkyl radical or together form a lower alkylene chain having from 2 to 4 carbon atoms, is subjected to the action of an ester of an aryl lower alkyl having the general formula III:

Ar—X—R—Y    III in which

Ar, X and R are defined as previously given, and Y is a halogen atom, or the acyl residue of a lower alkyl- or a phenylsulfonic acid, to produce an aryl lower alkyl piperidone of the general formula IV:

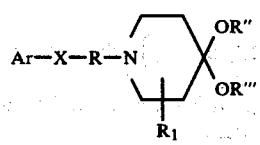

in which the substituents Ar, X, R, R₁, R" and R''' have the above-given definitions, hydrolyses the ketal function by means of an acid or by exchange of function with a carbonyl derivative in order to produce an (aryl lower alkyl) piperidone of the formula V:

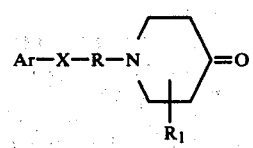

wherein Ar, X, R and R₁ are defined as previously given, reacts the latter with hydroxylamine to form the corresponding oxime of the general formula IV:

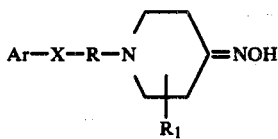

VI wherein the meanings of the substituents are the same as previously, reacts this oxime with a reducing agent selected from the group consisting of an alkali-metal mixed hydride and a metallic reducing agent, to produce a 4-amino piperidine of general formula VII:

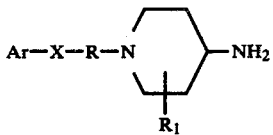

VII wherein the meanings of the substituents are defined as above, then condenses the 4-amino piperidine with an isatoic anhydride of the general formula VIII:

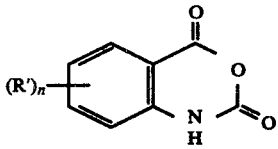

VIII in which R' and n are defined as above-given,
to form a substituted anthranilamide of the general formula IX:

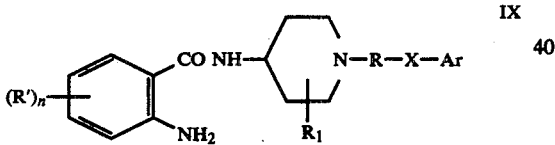

IX in which the substituents R', n, $R_1$, R, X and Ar are defined as previously given,
which is cyclised by heating with a lower alkyl carboxylic acid of the general formula X:

$R_2$—COOH   X in which $R_2$ is a hydrogen or a lower alkyl radical,
and recovers the (quinazolon-yl) piperidine of the general formula I, which may be further salified by adding a mineral or organic acid or resolved into its optically-active isomers when the molecule contains at least one asymetric carbon.

According to preferred features, the process of this invention may also defined as follows:

(a) the ester of aryl lower alkyl having the general formula III is a halide such as a bromide or a chloride, a methyl sulfonate or a p.toluene sulfonate.

(b) the condensation between the ketal of piperidone of general formula II and the ester of aryl lower alkyl is performed in an inert oxygenated solvent such as an alkyl ester of a lower alkyl carboxylic acid for example ethyl acetate; a linear or cyclic ether such as isopropylether or tetrahydrofuran, a carbonylated solvent for example acetone, methyl ethyl ketone or methyl isobutyl ketone.

(c) the condensation between the ketal of piperidone and the ester of aryl lower alkyl is performed in the presence of an agent able to bind the protons such as a dilower alkyl amine, a trilower alkylamine, a pyridine base, dimethyl acetamide, dimethyl formamide or a mineral basic agent for example an alkali metal carbonate or an earth-alkaline metal carbonate.

(d) the hydrolysis of the ketal function is carried out with a mineral or organic acid such as hydrochloric acid or acetic acid, by means of an ion exchange resin under acidic form such as a polystyrene sulfonic acid resin, or by exchange of function with a carbonyl-containing derivative such as formaldehyde in acidic medium, glyoxalic acid, pyruvic acid or γ-ketolevulinic acid.

(e) the oximation of the free piperidone is carried by means of hydroxylamine in acidic medium.

(f) the reduction of the oxime of general formula VI is carried out by means of an alkali metal borohydride, an alkali metal aluminum hydride or by catalytic hydrogenation in the presence of Raney Nickel.

(g) the reaction between the 4-amino piperidine of general formula VII and the isatoic anhydride having the general formula VIII is performed in an aprotic polar solvent such as pyridine, dimethyl formamide, dimethyl acetamide, dimethyl sulfoxyde or hexamethyl phosphortriamide.

(h) the cyclisation of the anthranilamide having the general formula IX is carried out by heating above 100° C. with the acid of general formula X.

According to another feature of the invention, the compounds of general formula I may also be produced by submitting a N-benzyl piperidine having the formula XI:

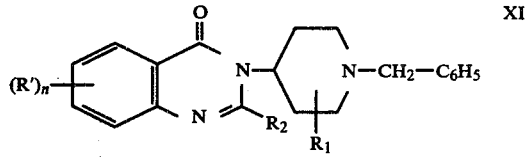

XI in which the substituents R', $R_1$, $R_2$ and n are defined as above-given,
to a debenzylation by means of catalytic hydrogenation or acid hydrolysis to produce a piperidine of general formula XII:

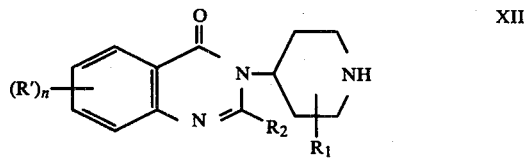

XII wherein the definitions of R', $R_1$ $R_2$ and n remain unaltered,
which is condensed with an arylalkyl ester of the formula XIII:

Ar—X—R—Z   XIII in which
Ar, X and R have the above-given definitions,
and Z is a halogen or the rest of an ester which may be easily split, to produce a compound of general formula I:

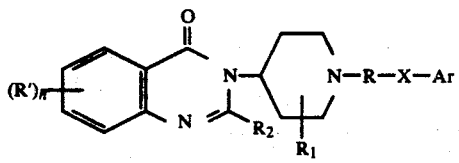

in which the definitions of the substituents remain unaltered,
which may further be salified by means of an organic or mineral acid, or resolved into their optically-active forms by reacting with an optically-active organic acid.

The compounds of general formula I may further be produced—when $R_2$ is a lower alkyl radical—by reacting a 4-amino piperidine of general formula VII:

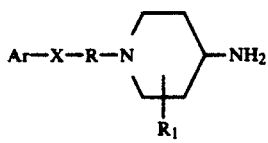

wherein the substituents Ar, X, R and $R_1$ are defined as above,
with a substituted anthranile of the formula VIII':

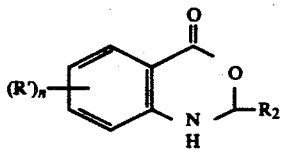

wherein
R' and n are defined as above,
and $R_2$ is a lower alkyl radical,
to produce a substituted anthranilamide of the formula IX':

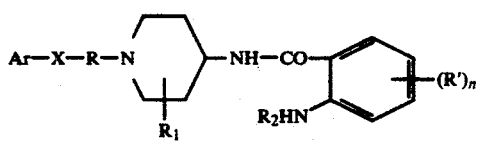

in which the definitions of the substituents is the same as above,
and cyclising the latter by heating into a compound of formula I in which $R_2$ is a lower alkyl, which may be when desired, converted into a salt resolved into their optically-active forms.

In this process, the reaction between the 4-amino piperidine of formula VII and the substituted anthranile of formula VIII' is performed in a high boiling solvent such as isoamyl alcohol, pyridine or collidine. The cyclisation of the substituted anthranilamide is carried out by heating it at a temperature ranging from 120° to 160° C.

Further both steps may be achieved in a single operation by heating the mixture of the compound of formula VII and the substituted anthranile of formula VIII in an oil-bath at a temperature ranging from 120° to 140° C. in the absence of a solvent.

This invention further extends to the novel compounds, intermediarily produced in or by the processes according to the invention:
(a) the quinazolinones of the formula XII:

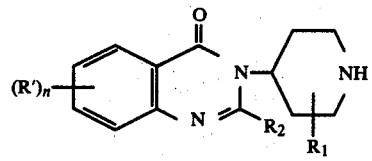

in which R', $R_1$, $R_2$ and n have the above-given definitions, and namely 3-(piperidino-4)4-oxo[3H]quinazoline.
(b) the anthranilamides of formula IX:

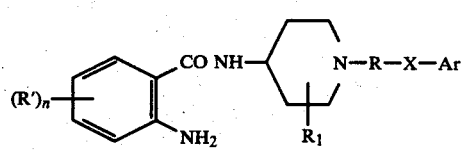

in which $R_1$, R', R, X, Ar and n have the above-given definitions, and namely 1-[2-(2,6-dimethylphenoxy)ethyl]4-N-(o.aminobenzamido)piperidine.

By the term "lower alkyl radical" there is meant an alkyl radical having from 1 to 6 carbon atoms in straight or branched chain. Examples of lower alkyl radicals are the methyl, ethyl, isopropyl, sec-butyl, neopentyl, tert-butyl and n-hexyl radicals.

By the term "lower alkenyl radical" there is meant an alkenyl radical having one or more double bonds and from 2 to 10 carbon atoms in straight or branched chain. Examples of lower alkenyl radicals are the allyl, methylallyl, isopentenyl, dimethyl-allyl, butenyl and triallyl-methyl radicals.

By the term "lower alkoxy radical" there is meant an alkoxy radical having from 1 to 6 carbon atoms.

By the term "lower alkynyl radical" there is meant an alkynyl radical having from 2 to 6 carbon atoms, for example an ethynyl, propyn-1-yl, propyn-2-yl or 1-methyl but-2-ynyl radical.

As mentioned above, the compounds of the general formula I which include at least one asymetric carbon may be resolved into their optical isomers by salification with an organic optically-active acid. Examples of suitable optically-active acids are d-tartaric acid, l-ketogulonic acid, ascorbic acid, l-menthoxyacetic acid, abietic acid, N,N-dimethyltartramic acid, d-camphosulphonic acid, d-glucose-1-phosphoric acid and d-glucose-1,6-diphosphoric acid.

The compounds of the general formula I may also be salified by adding a mineral or organic acid, preferably a physiologically tolerable acid. However, acids which are not physiologically tolerable form salts which may be useful for isolating, purifying or characterizing the compounds.

Examples of useful acids are hydrochloric, hydrobromic, hydroiodic, sulphuric, nitric, phosphoric and sulphurous acids; formic, acetic, valeric, lauric, benzoic, naphtoic, and pamoic acids; p-bromobenzenesulphonic, ethanesulphonic, isethionic and methanesulphonic acids; nicotinic, 5-methylthiazolcarboxylic, thienylcarboxylic and indolylacetic acids; and ethanol phosphoric acid.

The following examples are merely intended for the purpose of illustration. They do not limit the scope of the invention at all.

The temperatures are expressed in degrees Centigrade.

EXAMPLE I

1-[(2,6-dimethyl phenoxy)-2 ethyl]4-[4-oxo[3H]quinazolin-3-yl]piperidine

Step A: 8-[(2,6-dimethyl phenoxy)-2 ethyl]1,4-dioxa 8-aza[4,5]spiro decane

In a three neck flask, they are successively added 83.4 g of 2-(2,6-dimethyl phenoxy) 1-bromoethane, then 52 g of 1,4-dioxa 8-aza[4,5]spiro decane, 1500 ml methyl isobutyl ketone and 116 g dry potassium carbonate. The mixture is heated to reflux and kept under stirring for 24 hours, then let to revert to room temperature. The insoluble mineral matters are separated and the filter is rinced three times with methyl iosbutyl ketone. The organic phases are united, filtered again and evaporated to dryness. The residue weighs about 113 g and consists substantially of 8-[(2,6-dimethyl phenoxy)-2 ethyl]1,4-dioxa 8-aza[4,5]spiro decane. The compound is further purified by fractional distillation under 0.05 mm Hg. The desired compound boils at 150°–155° (yield 92.1 g i.e. 87% of the theory).

Step B: 1-[(2,6-dimethyl phenoxy)-2 ethyl]4-oxopiperidine

In a flask, they are suspended 92.1 g of 8-[(2,6-dimethyl phenoxy)-2 ethyl]1,4-dioxa-8 aza[4,5]spiro decane in 500 ml 4-N-hydrochloric acid solution. The mixture is heated to reflux for 2 hours then cooled to room temperature. The acidic solution is extracted twice with 50 ml ether; the aqueous phase is thereafter made alkaline with cautious addition of potassium hydroxyde and extracted three times with ether. The organic extracts are united, dried on sodium sulphate, filtered and evaporated off. The dry residue weighing 77.3 g is further purified by fractional distillation. The pure 1-[(2,6-dimethyl phenoxy)-2 ethyl]4-oxo piperidine distills at 150° under 0.05 mm Hg (yield 87.5% of the theory).

Step C: 1-[(2,6-dimethyl phenoxy-2)ethyl]4-oximido piperidine (hydrochloride)

20.2 g of hydroxylamine hydrochloride are dissolved in 50 ml water by warming. To this solution one adds a solution of 74 g of 1-[(2,6-dimethyl phenoxy)-2 ethyl]4-oxo piperidine in 50 ml ethanol. The whole mixture is heated to reflux for 30 mn giving a clear solution. After standing for 1 hour in a cool place, crystallization is initiated by scratching. The crystals are filtered, washed with 50 ml of a mixture water-ethanol twice, dried in an oven then under vacuum. Finally, they are recovered 70 g of the desired compound melting at 226° (yield 78.5% of the theory).

Step D: 1-[(2,6-dimethyl phenoxy)-2 ethyl]4-amino piperidine 70 g of the oxime (hydrochloride) of the step C are suspended in 250 ml ethanol and a solution made of 5.4 g sodium in 250 ml ethanol is portion-wise added hereto under cooling. After completion of the addition, the mixture is heated to reflux for 1 hour. After return to room temperature, the precipitate of sodium chloride is suction-filtered and the filtrate is evaporated off. The thus obtained crystals are taken up in 500 ml methanol. The methanolic solution is transferred into an autoclave, added with Raney Nickel and hydrogenated under a pressure of 100 kg/cm$^2$ at 70° for 12 hours. The day after, the precipitate of Raney Nickel is suction-filtered, washed many times with ethanol. The washings are added to the filtrate, and distilled off under reduced pressure. A yield of 65 g of raw product is thus obtained. The product is further purified by distillation under reduced pressure. It boils at 140° under 0.5 mm Hg. 38.2 g of 1-[2,6-dimethyl phenoxy)-2 ethyl]4-amino piperidine are recovered. By protometric titration, the purity of this amine is better than 99%. The overall yield is 65.5% of the theory.

Step E: 1-[2-(2,6-dimethyl phenoxy)ethyl]4-N-(o.amino benzamido)piperidine 8.5 g isatoic anhydride are dissolved in 25 ml dimethyl formamide. After completion of the dissolution, a solution of 12.4 g of 1-[(2,6-dimethyl phenoxy)-2-ethyl]4-amino piperidine in 60 ml methanol is added thereto portion wise. The whole mixture is heated at 45°–50° for 5 hours until the evolution of carbon dioxide ceased. The reaction mixture is thereafter poured into 210 ml water giving an oily insoluble residue. The mixture is made alkaline by adding few drops of sodium hydroxyde until the pH reaches the value of 9. The residue crystallizes after standing in a cool place. The crystals are suction-filtered, washed with water and dried in vacuo. 16.2 g of 1-[(2,6-dimethyl phenoxy)-2 ethyl]4-N-(o.amino benzamido)piperidine are obtained melting at 138°. The protometric titration indicates a purity of about 100%.

Step F: 1-[(2,6-dimethyl phenoxy)-2 ethyl]4-[4-oxo[3H]quinazolin-3-yl]piperidine 2.8 g of 1-[(2,6-dimethyl phenoxy)-2 ethyl]4-N-(o.amino benzamido)piperidine are dissolved in 30 ml formic acid and heated thereafter to reflux for 7 hours. After this time, the mixture is let to revert to about 60° and distilled off under reduced pressure. It remains an oily residue which is kept off in 5 ml of a 2 N solution of sodium hydroxide and few ml of ethyl ether. Crystallization soon initiates and the crystals are separted by filtration, dried, washed with water, then with ethyl ether and dried again. 1.9 g of 1-[(2,6-dimethyl phenoxy)-2 ethyl]4-[4-oxo[3H]quinazolin-3-yl]piperidine are thus recovered melting at 114°.

For analytical purposes, the compound is recrystalized from hot isopropanol giving 1.6 g of pure crystals melting at 118°. The yield is about 55%.

The compound is soluble in the stoichiometric amount of N/10 hydrochloric acid giving a solution of hydrochloride.

| Analysis | $C_{23}H_{27}N_3O_2 = 377,48$ | | |
|---|---|---|---|
| | C | H | N % |
| Found | 73.13 | 7.29 | 10.92 |
| Calculated | 73.18 | 7.21 | 11.14 |

EXAMPLE II

According to the same procedure, the following compounds have been obtained.

(a) 1-(3-phenyl propyl)4-[4-oxo[3H]quinazolin-3-yl]piperidine

M.P. 107°–108° C. (isopropanol)

The compound is soluble in aqueous solutions of methane sulfonic acid giving rise to the formation of methane sulfonate.

| Analysis | $C_{22} H_{25} N_3O$ = 347,46 | | |
|---|---|---|---|
| | C | H | N % |
| Calculated | 76.05 | 7.25 | 12.09 |
| Found | 76.21 | 7.53 | 12.16 |

(b) 1-(phenyl-2 ethyl)4-[4-oxo[3H]7-chloro quinazolin-3-yl]piperidine

M.P. 197°–198° (isopropanol)

| Analysis | $C_{21} H_{22} Cl N_3O$ = 367.88 | | | |
|---|---|---|---|---|
| | C | H | N | Cl % |
| Calculated | 68.56 | 6.03 | 11.42 | 9.64 |
| Found | 68.37 | 6.07 | 11.36 | 9.70 |

(c) 1-(phenyl-2 ethyl)-4-[4-oxo 6-methoxy[3H]quinazolin-3-yl]piperidine

M.P.=124° (isopropanol)

| Analysis | $C_{22} H_{25} N_3O_2$ = 363.46 | | |
|---|---|---|---|
| | C | H | N % |
| Calculated | 72.70 | 6.93 | 11.56 |
| Found | 72.90 | 6.88 | 11.49 |

(d) 1-(phenyl-2 ethyl)4-[4-oxo 6-chloro[3H]quinazolin-3-yl]piperidine

M.P. 160°–162° (isopropanol)

| Analysis | $C_{21} H_{22} Cl N_3O$ = 367.88 | | | |
|---|---|---|---|---|
| | C | H | N | Cl % |
| Calculated | 68.56 | 6.03 | 11.42 | 9.64 |
| Found | 68.57 | 5.89 | 11.32 | 9.57 |

(e) 1-benzyl 4-[4-oxo[3H]quinazolin-3-yl]piperidine

M.P.=147° (ethyl ether)

| Analysis | $C_{20}H_{21} N_3O$ = 319.4 | | |
|---|---|---|---|
| | C | H | N % |
| Calculated | 75.21 | 6.63 | 13.15 |
| Found | 74.83 | 6.65 | 13.10 |

(f) 1-(phenyl-2 ethyl)4-[4-oxo[3H]quinazolin-3-yl]piperidine

M.P.=145° (isopropanol)

| Analysis | $C_{21} H_{23} N_3O$ = 333.43 | | |
|---|---|---|---|
| | C | H | N % |
| Calculated | 75.65 | 6.95 | 12.60 |
| Found | 75.40 | 6.87 | 12.53 |

(g) 1-[(4-fluorophenyl)-2 ethyl]4-[4-oxo[3H]quinazolin-3-yl]piperidine

M.P.=179°–180° (isopropanol)

| Analysis | $C_{21} H_{22} F N_3O$ = 35.43 | | |
|---|---|---|---|
| | C | H | N % |
| Calculated | 71.77 | 6.31 | 11.96 |
| Found | 71.48 | 6.36 | 11.92 |

(h) 1-[(2,6-dimethyl phenoxy)-2 ethyl]4-[2-methyl[3H]4-oxo quinazolin-3-yl]piperidine (dihydrochloride)

M.P.=205° (ethanol)

| Analysis | $C_{24} H_{29} N_3O_2$, 2 Cl H = 464.44 | | | |
|---|---|---|---|---|
| | C | H | N | Cl % |
| Calculated | 62.06 | 6.73 | 9.05 | 15.27 |
| Found | 6.77 | 6.67 | 9.05 | 15.52 |

This compound retains 3% water as crystallization water.

EXAMPLE III

3-[2-(2,6-dimethyl phenoxy)ethyl piperidinyl-4]2-methyl 4-oxo[3H]quinazoline Starting from 1-[2-(2,6-dimethyl phenoxy)ethyl]4-amino piperidine produced at Step D of Example I and from 4.95 g acetyl anthranile heating at 135° in an oil-bath for 90 mn, 3-[(2,6-dimethyl phenoxy)ethyl piperidinyl-4]2-methyl 4-oxo[3H]quinazoline is obtained and further converted to its dihydrochloride which melts at 205° after recrystallization from ethanol.

The dihydrochloride is soluble in water.

| Analysis | $C_{24} H_{29} N_3O_2$, 2 ClH = 464.44 | | | |
|---|---|---|---|---|
| | C | H | N | Cl % |
| Calculated | 62.06 | 6.73 | 9.05 | 15.27 |
| Found | 61.77 | 6.67 | 9.05 | 15.52 |

EXAMPLE IV

3-(piperidinyl-4)[3H]4-oxo quinazoline

Starting from 4-benzylamino 1-(o.amino benzoyl)-piperidine produced as intermediate compound during the preparation of 1-benzyl 4-[4-oxo[3H]quinazolinyl-3]piperidine of example II(d) and performing the catalytic debenzylation by means of hydrogen in the presence of palladium on charcoal, 4-amino 1-(o.amino benzoyl)piperidine is obtained and the latter is cyclised into 3-(piperidinyl-4)4-oxo[3H]quinazoline by heating in formic acid at reflux temperature.

This compound is further purified by recrystallizing it from acetonitrile. It is slowly soluble in alkaline water at pH 9. It is soluble in dilute hydrochloric acid giving rise to the production of the hydrochloride.

| Analysis | $C_{13} H_{15} N_3O$ = 229.28 | | |
|---|---|---|---|
| | C | H | N % |
| Calculated | 68.10 | 6.59 | 18.32 |
| Found | 68.10 | 6.70 | 17.90 |

EXAMPLE V

1-[2-(4-oxo[3H]quinzolinyl-3)ethyl]4-[4-oxo[3H-]quinazolinyl-3]piperidine

Starting from 11 g 3-(piperidyl-4)4-oxo[3H]quinazoline and 12.4 g 2-(4-oxo[3H]quinazolin-3-yl)bromide, 1-[2-(4-oxo[3H]quinazolin-3-yl)ethyl]4-[4-oxo[3H-]quinazolin-3-yl]piperidine is obtained with a yield of 47%.

This compound is soluble in dilute solutions of hydrochloric acid.

EXAMPLE VI

1-[2-(indolyl-3)ethyl]4-[4-oxo[3H]quinazolin-3-yl]piperidine

Starting from 1-benzyl 4-amino piperidine obtained at example II(d) and acetic anhydride, 1-benzyl 4-acetyl amino piperidine is obtained. This compound is submitted to catalytic hydrogenolysis in the presence of pallidized charcoal. 4-acetyl amino piperidine is produced and further reacted with (indolyl-3 ethyl)bromide to form 1-[(indolyl-3)ethyl]4-acetylamino piperidine and the latter is hydrolysed in acidic medium to produce 1-[(indolyl-3)ethyl]4-amino piperidine which is reacted with isatoic anhydride according to the procedure of example I step E to produce the corresponding N-substituted anthranilamide which is cyclised into a quinazoline by heating in a mixture of formic acid and ethyl orthoformate.

1-[2-(indolyl-3)ethyl]4-[4-oxo[3H]quinazolin-3-yl]piperidine is a colourless solid melting at 189°–190° (from methanol).

It is soluble in a dilute aqueous solution of methane sulfonic acid.

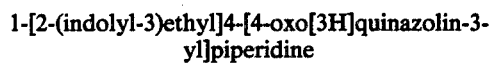

| | C | H | N % |
|---|---|---|---|
| Calculated | 74.16 | 6.50 | 15.04 |
| Found | 74.07 | 6.45 | 14.98 |

EXAMPLE VII

Using the same procedure as in Example I and starting from 4-phenyl butyl bromide and 1,4-dioxa 8-aza[4,5]spiro decane, 1-(4-phenyl butyl)[4-oxo[3H-]quinazolin-3-yl]piperidine is obtained which melts at 116°–118° (from isopropanol).

| Analysis | $C_{23}H_{27}N_3O = 361.49$ | | |
|---|---|---|---|
| | C | H | N % |
| Calculated | 76.42 | 7.53 | 11.62 |
| Found | 76.30 | 7.53 | 11.51 |

EXAMPLE VIII

Using the same procedure as in Example I, starting from [3-(m.trifluoromethylphenyl)propyl-2]1,4-dioxa 8-aza[4,5]spiro decane, dl-[3-(m.trifluoromethyl phenyl)propyl-2]4-[4-oxo[3H]quinazolin-3-yl]piperidine is obtained which melts at 144°–146° after recrystallization from isopropanol.

This compound is soluble in dilute aqueous solution of methane sulfonic acid.

| Analysis | $C_{23}H_{24}F_3N_3O = 415.44$ | | |
|---|---|---|---|
| | C | H | N % |
| Calculated | 66.50 | 5.82 | 10.11 |
| Found | 65.84 | 6.11 | 10.01 |

The starting material, 1-[3-(m.trifluoromethyl phenyl)propyl-2]1,4-dioxa 8-aza(4,5)spiro decane, is obtained by condensing 1,4-dioxa 8-aza(4,5)spiro decane with (m. trifluoromethyl benzyl)methyl ketone to produce the corresponding enamine which is reduced into 1-[3-(m.trifluoromethyl phenyl)propyl-2]1,4-dioxa 8-aza(4,5)spiro decane by means of sodium borohydride in aqueous solution.

EXAMPLE IX

Using the same procedure as in Example I and starting from 1-[4-(trifluoromethyl)3-phenylbutyl]bromide and 1,4-dioxa 8-aza(4,5)spiro decane, 1-(trifluoromethyl 3-phenyl butyl)4-[4-oxo[3H]quinazolin-3-yl]piperidine is obtained as the hemi hydrate, melting at 128°–129° (from isopropanol).

The starting material 1-[4-(trifluoromethyl)3-phenyl butyl]bromide is obtained as follows:

Step A: Ethyl 4-trifluoro 3-phenyl but-3-enoate

In a three-neck flask, 10.79 g of a 50% suspension of sodium hydride in mineral oil and few ml of perfectly dried diethylene glycol dimethyl ether (sold under the trade name of diglyme) are introduced, then slowly a solution of 42 g of ethyl diethoxy phosphonoacetate in 270 ml diethylene glycol dimethylether is added thereto while keeping the inner temperature below 35°. This addition takes more than 1½ hour. The stirring is continued until the evolution of hydrogen ceases. To the clear solution, a mixture of 26.1 g ααα-trifluoro acetophenone and 330 ml diethylene glycol dimethylether is added. The whole mixture is kept aside for one hour then heated to reflux for 8 hours under stirring. The mixture is let to revert to room temperature for a night and heated anew for 8 hours to reflux temperature. The mixture is thereafter cooled in a water-icebath and very slowly poured in an inert atmosphere in 230 ml water while keeping the inner temperature below +10°. The clear resulting solution is extracted twice with 200 ml ether each time. The etherous phases are separated, united, dried on sodium sulphate and evaporated off. The dry residue weighing 47.7 g is purified by fractionated distillation. Ethyl 4-trifluoro 3-phenyl but-3-enoate is a colourless liquid boiling at 60°–66°/0.05 mm Hg (yield=30.6 g).

Step B: Ethyl 4-trifluoro 3-phenyl butyrate

In a stainless steel recipient under pressure, they are successively charged 30 g ethyl 4-trifluoro 3-phenyl but-3-enoate, 110 ml ethanol and 1.5 g 5% palladized charcoal. The atmospheric oxygen is expelled through bubbling of nitrogen then the hydrogenation is performed under a pressure of 4 kg/cm² at 40°–60°. After 3 hours the absorption of hydrogen ceases. The mixture is kept aside for a night. The catalyst is thereafter succion-filtered and washed with ethanol. The filtrates are gathered and distilled off producing an oily residue weighing 28 g. Ethyl 4-trifluoro 3-phenyl butyrate is a thick colourless liquid, soluble in ethanol. It is used as such for the next step of the synthesis.

Step C: 4-trifluoro 3-phenyl butanol

A mixture of 5.95 g lithium alumino hydride in 60 ml ether is obtained by cautious addition of the solid thereto while cooling to −10°. Once the mixture homogeneous, 26 g of ethyl 4-trifluoro 3-phenyl butyrate in 60 ml ether is added dropwise while keeping the temperature of the mixture below 0°. After completion of the addition, the mixture is stirred for 1 hour then let to revert to room temperature. Excess of reagent is destroyed by cautious addition of 40 ml of a solution of tartaric acid in water then 30 ml of saturated solution of sodium chloride. The insoluble matters are filtered then the etherous phase is separated, washed with water, dried and evaporated off.

18.3 g of an oily residue is thus recovered and further purified by fractional distillation. The yield in 4-trifluoro 3-phenyl butanol amounts to 85.5%. The pure product boils at 126°-129°/18 mm Hg.

Step D: 4-trifluoro 3-phenyl 1-bromo butane 18 g of 4-trifluoro 3-phenyl butanol are dissolved in 100 ml ether and the solution is cooled to 0° by immersion in a water-ice bath. To the cool solution, a solution of 11.7 g phosphorous tribromide in 40 ml ether is added very slowly while maintaining the inner temperature between 0° and 5°. After completion of the addition, the temperature is let to revert to room temperature then after one hour of contact, the mixture is poured on crushed ice. The suspension is extracted many times with ether. The organic solutions are united, washed with water, dried and evaporated off. 15.8 g of 4-trifluoro 3-phenyl 1-bromobutane are recovered and used as such for the next step of the synthesis.

EXAMPLE X

Injectible solution containing 5 mg of 1-[2-(2,6-dimethyl phenoxy)ethyl]4-[4-oxo[3H]quinazolinyl-3]piperidine as its hydrochloride per unit dosage

| Active ingredient | 50 g |
| --- | --- |
| Sodium chloride | 40 g |
| Malic acid | 10 g |
| Glycine | 12 g |
| Water | 20 000 ml |

This solution is divided out in 10,000 ampuls of 2 ml each after having be filtered on a sterilizing filter. The ampuls are further sterilized by heating at 120° for 20 minutes.

EXAMPLE XI

Pharmacological study of the compounds according to the invention (a) Determination of the acute toxicity The acute toxicity of the compounds of general formula I has been determined in batches of 10 mice (Swiss strain) weighing each about 20 g. They received increasing dosis of the tested compound intraperitoneously. The administered dosis ranged from 25 to 200 mg/kg. The animals are kept under survey for 8 days and the deaths, if any, are numbered.

The average lethal dosis, graphically calculated, is usually between 50 and 100 mg/kg. For some compounds, no mortality is observed at 100 mg/kg and the average lethal dosis is far superior. At the toxic dosis, the only symptoms are sedation then convulsions.

(b) Determination of the hypotensive activity

The hypotensive activity of the compounds of general formula I has been ascertained in the dogs, which have previously been anaesthetized with Nembutal.

In the same time, the carotidal pressure and the cardiac performances are recorded immediately before the intravenous injection of the compound to be tested and for a period of time extending over 4 hours after.

Dosis of 0.5 and 1 mg/kg induce a decrease of 20% of mean arterial pressure without exerting any effect on the cardiac rhythm.

Dosis of 2 mg/kg leads to a decrease of 30–35 mm Hg of the mean arterial pressure and the cardiac rythm is decreased by about 30%. The duration of this effect extends for about 4 hours. At these dosis, the respiratory output is only slightly decreased. At the contrary, for some compounds it is even significantly increased (50% of the initial volume for more than one hour).

The hypotensive action has also been studied in the dogs which have been made hypertensive by nephrosclerosis. Dosis of 1 mg/kg by intravenous way induce a transient increase of the arterial pressure followed by a significant decrease lasting about 4 hours. The cardiac rythm is also increased during the same period of time.

The compounds of general formula I have been also tested in the presence of the usual chemical mediators (Adrenaline, Nor Adrenaline, Serotonine, Tyramine, Histamine, DMPP). The hypertensive action of these mediators is significantly counteracted or even antagonized by injection of the compounds according to the invention.

(c) Search of a neurological effect

In the mice the first active dosis is 10 mg/kg. At this dose by intraperitoneous way, it may be shown a slight ptosis. At 20 mg/kg, the mice show a slight decrease in the muscular tone and in the reflexes. The walking is slightly jerky. A dosis of 50 mg/kg induces convulsions. The motility is just decreased.

In the rats, an intraperitoneous injection of 50 mg/kg leads to convulsive tremors. The motility and the respiration are slightly depressed. The animals show some ptosis.

The neurological symptoms are very discrete and appear only at sub-toxic dosis.

The starting material 1,4-dioxa 8-aza[4,5]spiro decane may be obtained according to the process described by J. Mac Manus [J. Mad. Chem. 8 766 (1965)].

The starting aralkyl esters of formula III are obtained according to the processes described in the french patent application 76.12671 filed on April 29, 1976 under the title: "Nouvelles 4-amino piperidines, leurs procedes d'obtention et les compositions pharmaceutiques en renfermant" and in the British patent application 49 540/75 filed on Nov. 14, 1975.

What we claim is:

1. The 4-[4-oxo-(3H)-quinazolin-3-yl]N-aralkyl piperidines of the formula

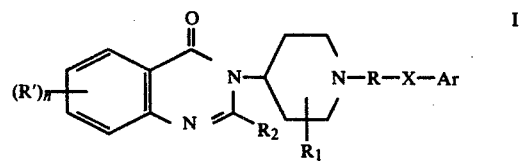

wherein Ar is:

(1) the thienyl radical (2) phenyl or substituted phenyl having the formula

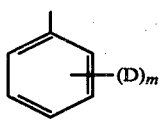

wherein D is selected from the group consisting of halogen, lower alkyl, lower alkoxy, lower alkenyloxy, lower alkynyloxy, lower alkylthio, carboxyl, lower alkoxycarbonyl, nitro, amino, (lower alkyl) amino, lower alkylcarbonylamino, sulphamido, lower alkylamino sulfonyl, di(lower alkyl)-amino sulfonyl, lower alkyl sulfonyl, amino carbonyl, cyano, and trifluoromethyl; and m is an integer from zero to five, inclusive;

(3) a heterobicyclic radical having the formula:

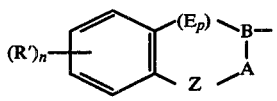

wherein R' is a radical selected from the group consisting of hydroxyl, lower alkoxy, lower alkylenedioxy, halogen, trifluoromethyl, trifluoromethoxy, trifluoromethylthio, nitro, amino, phenyl, and phenyl lower alkyl, Z is the imino nitrogen —N=,
A is an unsubstituted methylidene or methylidene radical substituted with a lower alkyl,
B is the imino group

E is carbonyl, and
p is 1
either Z is the imino group

A and B together are an ethylidene radical, E is methylene, and p is zero or 1;
or Z is the imino group

E is a methylene, p is zero or 1, A is carbonyl, and B is the imino nitrogen

or A and B together are an ethylene radical,
X is an oxygen atom, a sulphur atom, or an imino radical of the formula:

wherein Y is hydrogen, lower alkyl, lower alkenyl or lower alkoxy carbonyl, or X is a methylene radical or a direct carbon-carbon bond,
R is an alkylene radical having 1 to 4 carbon atoms, optionally substituted with a lower alkyl radical or a trifluoromethyl radical,
$R_1$ is a hydrogen or a lower alkyl radical,
$R_2$ is a hydrogen or a lower alkyl radical, and
n is an integer of zero to 3
including acid addition salts thereof.

2. The compounds according to claim 1, wherein R is an alkylene radical having from 1 to 4 carbon atoms optionally substituted with a lower alkyl radical.

3. The salts of a compound of claim 1 with a therapeutically compatible acid.

4. The optically active isomers of the compounds of claim 1, when the chemical structure includes at least one asymmetric carbon.

5. A compound of claim 1, in which Ar is the thienyl radical having the formula $I_A$

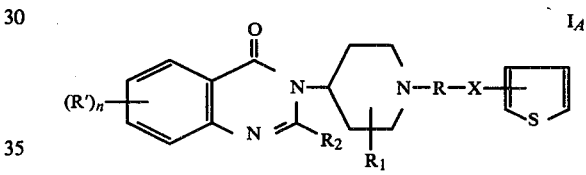

6. A compound of claim 1, in which Ar is phenyl or substituted phenyl.

7. dl 1-[4-trifluoro 3-(phenyl butyl)]4-[4-oxo[3H-]quinazolin-3-yl]piperidine, according to claim 6.

8. 1-(2-phenyl butyl) 4-[4-oxo[3H]quinazolin-3-yl]piperidine, according to claim 6.

9. 1-[3-(m.trifluoromethyl phenyl)propyl-2]4-[4-oxo[3H]quinazolin-3-yl]piperidine, according to claim 6.

10. 1-[2-(2,6-dimethyl phenoxy)ethyl]4-[6-chloro 4-oxo[3H]quinazolin-3-yl]piperidine, according to claim 6.

11. dl 1-(2-phenyl 1-methyl ethyl) 4-[4-oxo[3H-]quinazolin-3-yl]piperidine, according to claim 6.

12. 1-[2-(4-fluorophenyl)ethyl]4-[4-oxo[3H]quinazolin-3-yl]piperidine, according to claim 6.

13. 1-(3-phenylethyl) 4-[4-oxo 6-methoxy[3H-]quinazolin-3-yl]piperidine, according to claim 6.

14. A compound of claim 1, in which Ar is a quinazolinonyl ring having the formula $I_C$:

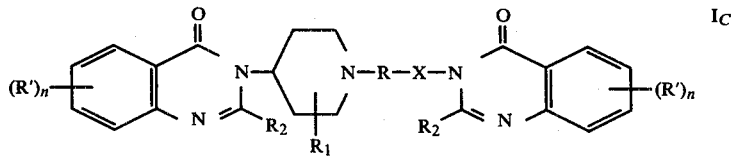

15. A compound of claim 1, in which Ar is an indolyl ring having the formula $I_D$:

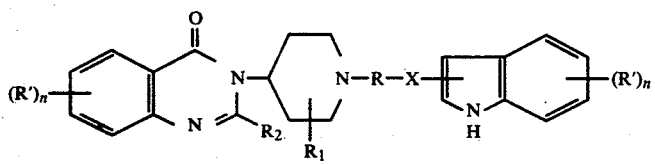

16. A compound according to claim 15 which is: 1-[2-(indolyl-3)ethyl]4-[4-oxo[3H]quinazolin-3-yl]piperidine.

17. A compound of claim 1, in which Ar is a benzimidazolonyl ring having the formula $I_E$:

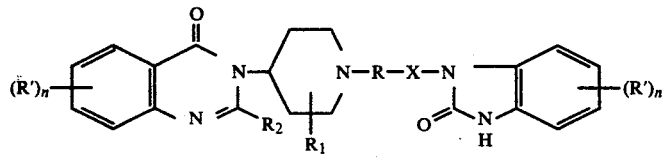

18. The pharmaceutical compositions including as active ingredient at least one compound of claim 1 in an amount effective for treating hypertension, in admixture with an inert non toxic pharmaceutically-acceptable carrier.

19. A pharmaceutical composition intended for parenteral, oral, sublingual or rectal administration, according to claim 18.

20. A pharmaceutical composition according to claim 18 in which the amount of active ingredient ranges from 5 to 50 mg per unit dosage.

21. A method for treating hypertension in patients suffering from hypertension, without inducing depression on the Central Nervous System which consists in administering to said patients an amount safe and effective for improving said condition, of a compound of claim 1.

22. The method of claim 21 in which the amount of the essential-active ingredient ranges from 0.08 to 1.5 mg/kg per day.

23. The 4-[4-oxo-(3H)-quinazolin-3-yl]N-aralkyl piperidines of the formula

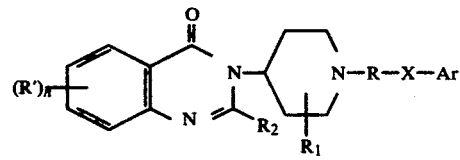

wherein Ar is:
(1) the thienyl radical
(2) phenyl or substituted phenyl having the formula

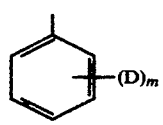

wherein D is selected from the group consisting of halogen, lower alkyl, lower alkoxy, lower alkenyloxy, lower alkynyloxy, nitro, sulfamido, cyano, amino, and trifluoromethyl; and m is an integer from zero to five, inclusive;

(3) a heterobicyclic radical having the formula:

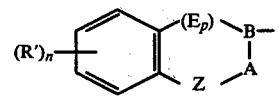

wherein R' is a radical selected from the group consisting of hydroxyl, lower alkoxy, lower alkylenedioxy, halogen, trifluoromethyl, trifluoromethoxy, nitro, and amino;

Z is the imino nitrogen —N=, or the imino group

B is the imino nitrogen

A is carbonyl unsubstituted methylidene, or methylidene substituted with a lower alkyl group; A and B taken together are ethylidene or ethylene, (E) is carbonyl or methylene, and p is zero or one;

X is an oxygen atom; a sulphur atom; an imino radical of the formula

wherein Y is hydrogen, lower alkyl, lower alkenyl, or lower alkoxy carbonyl; the methylene radical; or a direct carbon-carbon bond, R is an alkylene radical having 1 to 4 carbon atoms, optionally substituted with a lower alkyl radical or a trifluoromethyl radical, $R_1$ is a hydrogen or a lower alkyl radical, $R_2$ is a hydrogen or a lower alkyl radical, and n is an integer from zero to three including acid addition salts of the described free base compounds.

* * * * *